US00PP08673P

United States Patent [19]

Waliser

[11] Patent Number: Plant 8,673

[45] Date of Patent: Apr. 5, 1994

[54] APPLE TREE WALISER GALA

[75] Inventor: H. Kent Waliser, Milton-Freewater, Oreg.

[73] Assignee: H. K. Waliser, Milton-Freewater, Oreg.

[21] Appl. No.: 816,656

[22] Filed: Jan. 3, 1992

[51] Int. Cl.[5] ..... A01H 5/00

[52] U.S. Cl. ..... Plt./34.1

[58] Field of Search ..... Plt. 34.1

*Primary Examiner*—James R. Feyrer

*Attorney, Agent, or Firm*—Chernoff, Vilhauer, McClung & Stenzel

[57] ABSTRACT

A new variety of apple originating as a whole-tree mutation of its parent variety Royal Gala (Tenroy cultivar, U.S. Plant Pat. No. 4,121) selected particularly for its early red skin color and the unique overall pinstripe color pattern of its fruits.

5 Drawing Sheets

BACKGROUND AND SUMMARY OF THE INVENTION

This invention relates to a new and distinct variety of apple tree, and more particularly to a whole-tree sport mutation of the apple variety known as the Tenroy cultivar of red Gala (U.S. Plant Pat. No. 4,121).

The discovery of the new variety was made by the inventor, Mr. Kent Waliser, in early August 1988 in one of his cultivated red Gala apple orchards located at Route 2, Box 357, Milton-Freewater, Oreg.

The inventor was attracted to the new red Gala sport by the early, bright, cherry-red, pinstripe coloring pattern of its fruits. The trees in the orchard where the new sport was discovered were planted in the spring of 1986 on M-7A rootstock and produced a first crop of fruit in 1988. Prior to fruiting, no noticeable differences in tree growth, vigor, etc. has been noted. Upon fruiting, the new sport exhibited fruit that had a different, more full-red, pinstripe color pattern than the fruit on the other Waliser trees in the orchard. The newly discovered cultivar was named Waliser Gala.

Asexual reproduction of the Waliser Gala was successfully accomplished in early September 1988 at which time second generation trees were grafted. Three hundred second generation trees were planted at an orchard site near Milton-Freewater, Oreg. on M-7A rootstock in the spring of 1991.

All of the fruit borne on the three hundred second generation trees have been identical to the fruit borne on the original whole-tree sport which is now six years old and is located in an adjacent orchard. All of the second generation fruit has exhibited the same bright cherry-red pinstripe fruit skin coloration and has retained the taste of the Royal Gala.

The inventor, who is a member of the Pacific Northwest Fruit Testers Association, 1101 W. Orchard Avenue, Selah, Wash. 98942, maintains over 40 apple cultivars in his variety evaluation test site, located at Route 2, Box 357, Milton-Freewater, Oreg. 97862. Included in this test block are the following cultivars of red sports of Gala:

1. Creech cultivar of Red Gala (Scarlet Gala) U.S. Plant Pat. No. 6,172;
2. Treeco Spur Red Gala #42 (herinafter Regal) U.S. Plant Pat. No. 7,396; and
3. Fulford cultivar of Red Gala (hereinafter Regal Gala) U.S. Plant Pat. No. 7,589.

These three patented and commonly available Red Gala cultivars and their fruits have been intensively evaluated and compared to the WALISER GALA and to each other by the inventor at his test site near Milton-Freewater. The new variety has also been compared directly to other unnamed (numbered) selections of Red Gala growing in the inventor's test block. These unnamed, unidentified selections consist of several early coloring sport clones which have been observed in the inventor's orchards near Milton-Freewater and trees of each have been propagated and added to the test site for observation and evaluation. Though trees of Galaxy Gala (U.S. Plant Pat. No. 6,955) are now offered for sale commercially in the United States, no direct comparison of this new variety could be made to our new Waliser Cultivar. The Galaxy Gala was discovered in 1985 in New Zealand and trees have only just recently been offered for sale in the United States.

All evaluations of our new variety have been conducted and recorded in the Milton-Freewater, Oreg. area (Walla Walla Valley) in the inventor's commercial and/or test orchards and reflect the growing conditions common to the area since our new cultivar has not been grown and/or come into production in other apple growing districts of the Northwest, a broad range of characteristics as it may relate to other geographical areas, could not be made.

The Milton-Freewater apple district is considered to be an early fruit maturing district with an abundant summer sun and high summer temperatures which occasionally reach 100+ degrees Fahrenheit in the midsummer months of July and August. Red color formationon red varieties of apple fruits is not as intense in this district as found on trees which are planted and grown in some of the cooler mountain valley apple growing districts of the Pacific Northwest where a deeper shade of red color may develop later in the season.

The Waliser Gala cultivar has been carefully compared to its parent, the Royal Gala cultivar, and to the red Gala cultivars, established in the inventors' test site near Milton-Freewater.

Fruit color, color intensity, fruit maturity and growth characteristics of our new variety are compared to the varieties listed above and to the parent cultivar (see Table 1).

TABLE 1

Color and Growth Characteristics of Red Gala Cultivars for Harvest year 1992 (Milton-Freewater, Oregon)

| | Trait | | | |
|---|---|---|---|---|
| Variety | Color | Type Growth | Spur Density* | Color Intensity ** (%) |
| Royal | broad stripe | standard | 21.5 | 65 |
| Scarlett | broad stripe | standard | 14.6 | 80 |
| Fulford | blush | standard | 20.6 | 100 |
| Treeco | stripe | spur | 27.1 | 85 |
| Waliser | narrow pinstripe | standard | 19.5 | 95 |

*Spurs per square centimeter of branch cross-sectional area.
**% red color (40-12) on August 15, 1992 as measured by the Munsell Color Cascade Chart and determined by measuring color on all fruits produced on five young test trees growing in inventor's test block.

The following differences have been noted and are hereby described:

Waliser Gala shows a much earlier red color characteristic than either the parent Royal Gala or the Scarlet Gala and about 10 days ahead of the Royal Gala. The earlier red color characteristic results in the need for fewer pickings to harvest the crop (see Table 2).

TABLE 2

Color Comparison for 1992 (Early Maturing Year) (Typical of Gala Strains)

| | Percent of Fruit Surface Covered by Color | | | |
|---|---|---|---|---|
| Variety | 7-21-92 | 8-1-92 | 8-7-92 | 8-15-92 |
| Royal | 10 | 10 | 50 | 60 |
| Scarlet | 25 | 30 | 65 | 60 |
| Fulford | 65 | 80 | 95 | 100 |
| Waliser | 45 | 60 | 75 | 90 |

Scarlet Gala begins coloring with a distinctive, broad pink to reddish stripe over a greenish-yellow ground color. Late in the harvest season, the Scarlet Gala finishes off with broad chimera-like stripes being common. Observations of Gala and Red Delicious cultivars in the Milton-Freewater, Oreg. area have shown that chimera-like striping is common on fruits which display a broad striping characteristic. In comparison, WALISER GALA begins coloring much earlier in the season with a bright luster-like cherry-red finish with very prominent, narrow, slight pinstripes, even on shaded sides of fruit. Fruits exposed to full sun and left on trees into the late Gala season may exhibit less pinstriping. Though less red pinstripe effect may be noted on such fruits, the overall effect is always present and underlies the fruit color pattern.

The above-mentioned pinstripe effect is particularly noticeable when Waliser Gala fruit is displayed in packed cartons or boxes. This color pattern differs distinctly from displays made up of blush (block colored) fruits. The value of this pinstripe characteristic is of considerable importance when marketing the fruit since striped red apple fruits are now preferred in many world markets over blush (block colored) red fruits. The value of this characteristic is particularly demonstrated in some years in poor coloring areas such as the Milton-Freewater district. The poorly colored striped apples are always preferred over the equally poorly colored solid red (block colored) apples produced in this and similar poor coloring districts.

Waliser Gala exhibits more red surface than its parent Royal Gala cultivar and ripens about three-four days ahead of the Royal Gala (see Table 3).

TABLE 3

| | | Matruity Comparison | | | |
|---|---|---|---|---|---|
| Variety | Harvest Date | Pressure | Soluble Solids | Starch* | Color (%) |
| Royal Gala | 9-14-88 | 17 | 15.5 | 2.5 | 70 |
| Waliser | 9-14-88 | 17.5 | 17 | 3.0 | 95 |

*The starch iodine test is used to determine the rate of apple maturation. The Golden Delicious comparison chart, which was used, was taken from the fruit maturity data system developed by Stemilt Testing Laboratory of the State of Washington. Data collected are the average values for 10 apples from each cultivar selected at random.

In comparing the Waliser Gala with the Regal Gala the following was noted: the Regal Gala variety exhibits an early bright red fruit factor slightly more intense than the Waliser Gala, but distinctly differs in its color pattern. The Regal Gala variety exhibits a uniform, bright red, blush (block) color pattern and show no striping at all, a distinct difference from the narrow pinstripe color characteristics of the Waliser Gala.

No direct comparison can be made to the Galaxy Gala (U.S. Plant Pat. No. 6,955) in the inventor's test block or in established orchards in the Milton-Freewater district. The following comparison using available written descriptions is hereby made. In reference to its patent description, the Galaxy Gala is described as follows:

1. "Possesses a solid cherry red coloration with indistinct darker red overstriking. Accordingly, the fruit exhibits a solid block red appearance over the entire fruit surface."

2. "More specifically, the fruit of the Galaxy variety exhibits a solid and intense cherry red coloration with darker red overstriking often having indistinct borders."

By comparison, our new variety has no tendency toward "solid and/or solid block red color as described in the Galaxy Gala patent described in the Galaxy Gala patent description.

The red pinstriped fruit skin color of Waliser Gala occurs prior to fruit maturity. Waliser Gala fruits attain their narrow pinstripe color pattern while the fruit flesh color is a pale green to white color (22-1 by Munsell Color Cascade Chart). All other Gala strains tested exhibits a more yellow, matrue flesh color (24-1 to 25-2 by Munsell Color Cascade Chart) as the fruit skin color changed to red is a pale green to white color (22-1 by Munsell Color Cascade Chart). All other Gala strains tested exhibited a more yellow, mature flesh color (24-1 to 25-2 by Munsell Color Cascade Chart) as the fruit skin color changed to red.

The Waliser Gala has growth characteristics similar to the Royal Gala, Scarlet Gala, and Regal Gala cultivars, exhibiting an open, standard type growth pattern. The Waliser Gala differs from the Cooper cultivar which has distinct spur-like growth characteristics. The spur-type growth characteristics of the Cooper cultivar results in a nonstandard compact tree (see Table 1).

Fruit color characteristics of the Waliser Gala appear to be somewhat similar to the Cooper cultivar in that both varieties color early with a red striped finish although the fine pinstriping in the Cooper cultivar is less pronounced.

No noticeable differences have been observed in fruiting habit between Waliser Gala and its parent Royal Gala cultivar. Precocity and response to chemical thinning are similar. No noticeable significant differences were recorded and/or observed in fruit size between all clones of red Gala tested in the inventor's test block.

Since Waliser Gala possesses standard nonspur growth characteristics, a variety of tree training methods can be employed such as:

1. Freestanding central leader training with trees on either seedling or dwarfing type rootstocks.

2. Central axis training with either pole or wire support on dwarfing type rootstocks.

3. Trellis-type training methods may be employed where more vagarious, nonspur type growth is necessary for proper training on dwarfing type rootstocks.

As is common with many super red sports of red apple cultivars, leaves of the Waliser Gala are a slightly darker green color when compared to leaves on immediately adjacent similar ages Tenroy trees grown under similar growing conditions, pruning, nitrogen, water, etc. This slight difference in green color shade is too slight to establish on color chart used.

Similarly, the pinkish-red color of some of the leaf petioles and midribs of the Waliser Gala is slightly more pronounced, and intense and often extends further down the midrib than red color on leaf petioles and midribs produced on trees of its parent Tenroy cultivar planted immediately adjacent to each other.

No other bark and/or tree growth differences have been noted.

Waliser Gala and the other red Gala cultivars tested have shown similar abilities to withstand winter freezes and spring frosts. All varieties experienced sub-zero temperatures in the winters 1989–90 and 1990–91 without showing any adverse effects.

Like Tenroy and the other clones tested, the skin of the Waliser Gala has shown no russet problems.

Waliser Gala appears to be free of virus and virus-like diseases such as Apple Mosaic, Green Crinkle, Russet Ring, etc., and is resistant to common fungal and bacterial diseases.

BRIEF DESCRIPTION OF THE DRAWINGS

The accompanying full color pictures illustrate our new Waliser Gala apple tree and its fruit and growth characteristics.

DETAILED DESCRIPTION OF THE INVENTION

The following is a detailed description of the new variety with color terminology in accordance with the Munsell Color Cascade Chart except where general color terms of ordinary dictionary significance are used.

Parentage: A whole-tree sport of the apple variety Royal Gala (Tenroy cultivar U.S. Plant Pat. No. 4,121).

Locality where grown and observed: Milton-Freewater area of Northeastern Oregon, U.S.A.

Dates of first and last pickings on normal years: About August 18 and August 28, respectively, in the Milton-Freewater area.

Tree: Medium small, spreading, round topped, hardy, productive, regular bearer, wide branch angles, nonspur type growth.

*Trunk.*—Medium stocky, smooth.

*Branches.*—Medium thickness, smooth, moderately branched. Color: Grey (3-1). Lenticels: Numerous, medium large.

*Leaves.*—Medium large, medium wide, medium long, oval, abruptly pointed smooth, medium thick. Color: Upper surface olive green (20-14), lower surface green (21-13). Length: From about 10.5 to 13 cm. Width: From about 5 to 7 cm. Margin: Crenate, finely serrate. Petiole: Long (from about 3.2 to 4.5 cm), medium slender, pubescent. Midrib: Pink at base, green near tip.

*Flowers.*—Medium early. Dates of first and full bloom: About April 22 and May 2, respectively. Size: Medium small (avg. 3.1 cm in diameter when fully open). Petals: Simple row, margin smooth, middle indentation slight. Color: White with pink on reverse side. Stamens: One distinct whorl, filaments white, anthers yellow. Pistils: Stigma prominent, stiles fused toward base, pubescent. Sepals: Large, pointed, thick.

Figure 1:
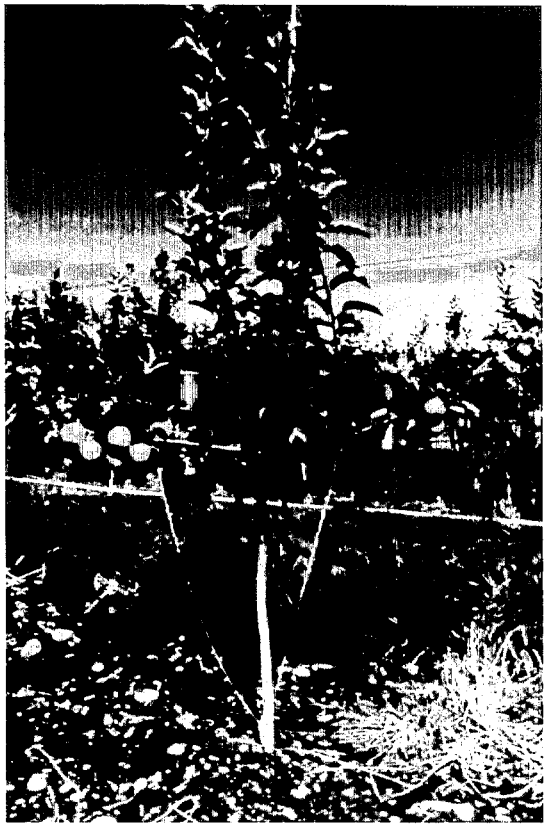
FIG. 1 shows a two year old second generation Waliser Gala tree with its first crop of fruit.
Figure 2:
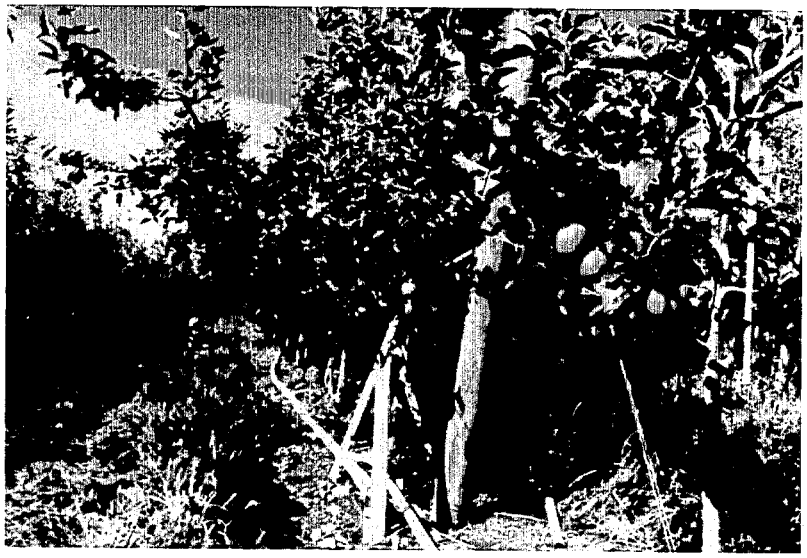
FIG. 2 shows a young two year old second generation Waliser Gala tree (front) and older sixth leaf Royal Gala (Tenroy cultivar) trees (back).
Figure 3:
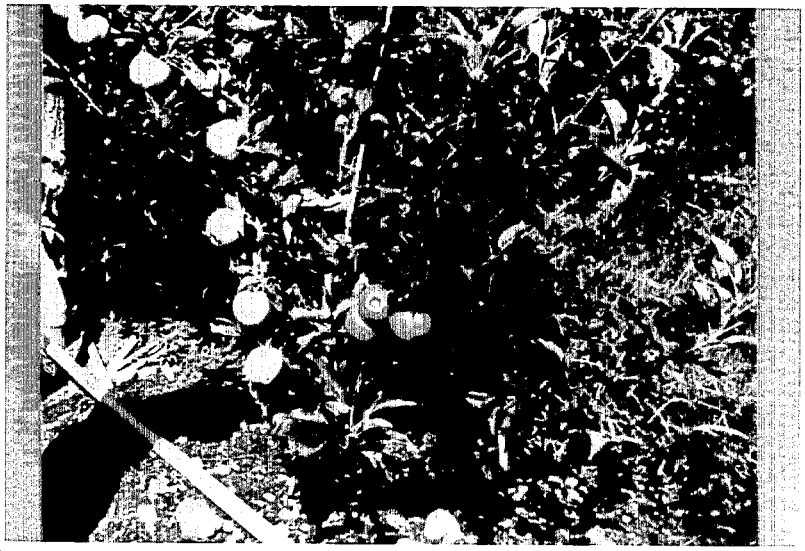
FIG. 3 shows the very distinct early fruit color character of Waliser Gala (front and right) when compared to its parent Royal Gala (left).
Figure 4:
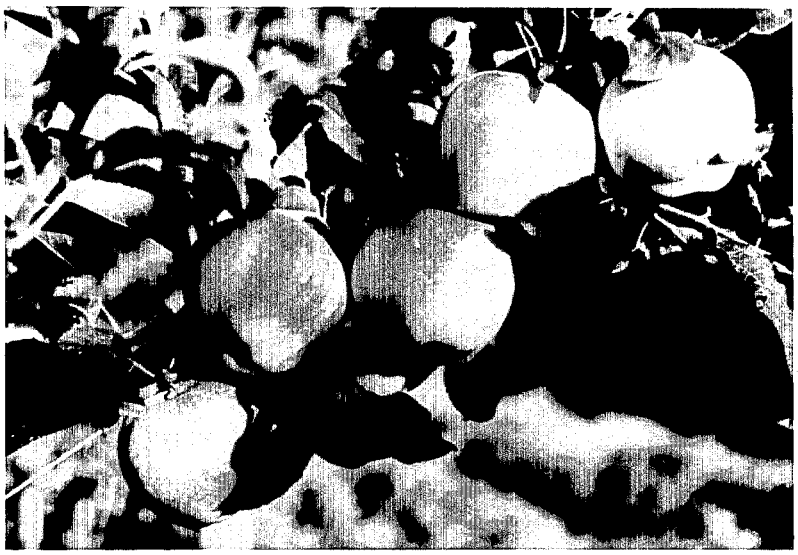
FIG. 4 shows the chimera-like red color patterns on Scarlet Gala fruits taken from third leaf trees.
Figure 5:
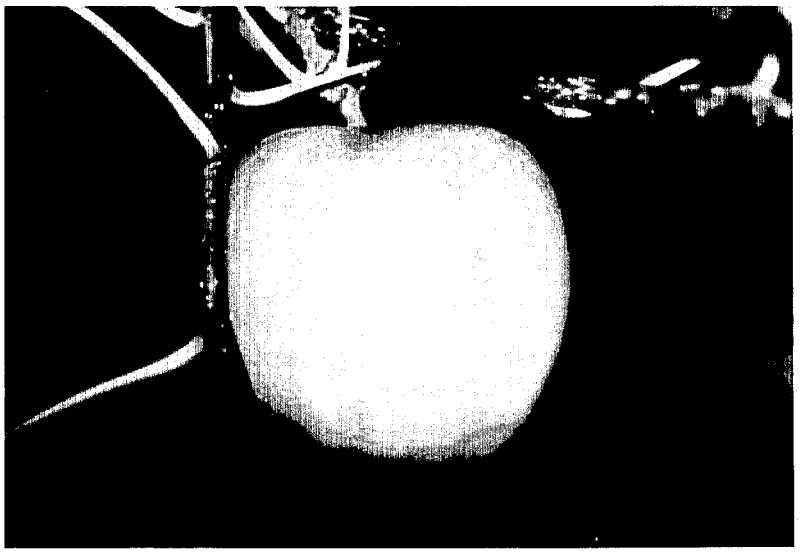
FIG. 5 shows the early, red, pinstripe color formation over greenish-yellow ground on Waliser Gala approximately twelve days before harvest.
Figure 6:
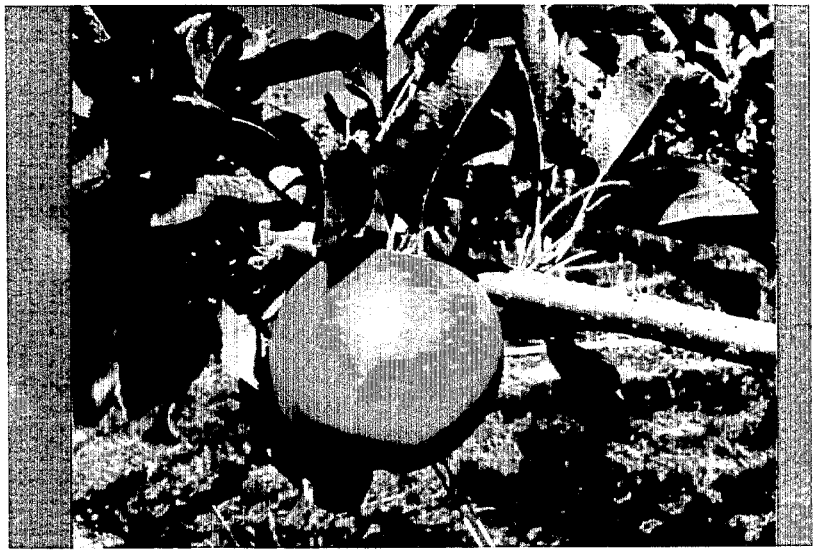
FIG. 6 show Waliser Gala ready for harvest.
Figure 7:
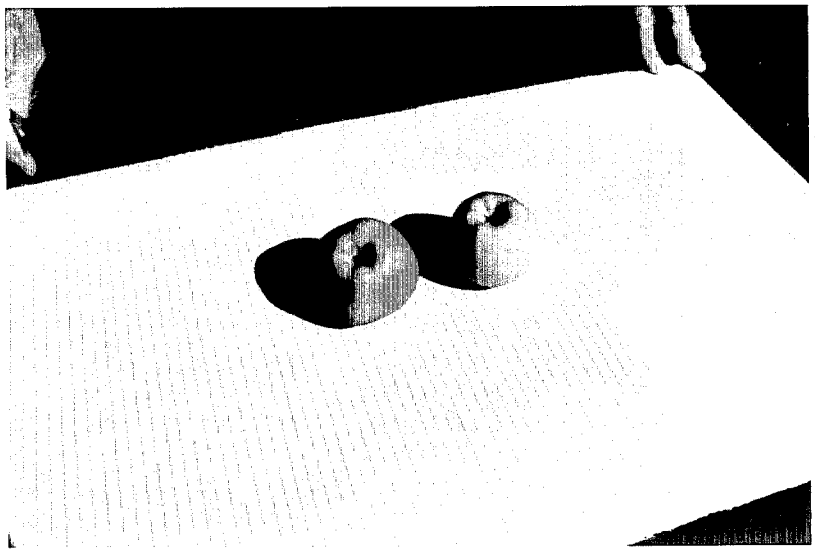
FIG. 7 shows early, full red color of Waliser Gala (left) versus spotty, light red color of its parent (right).
Figure 8:
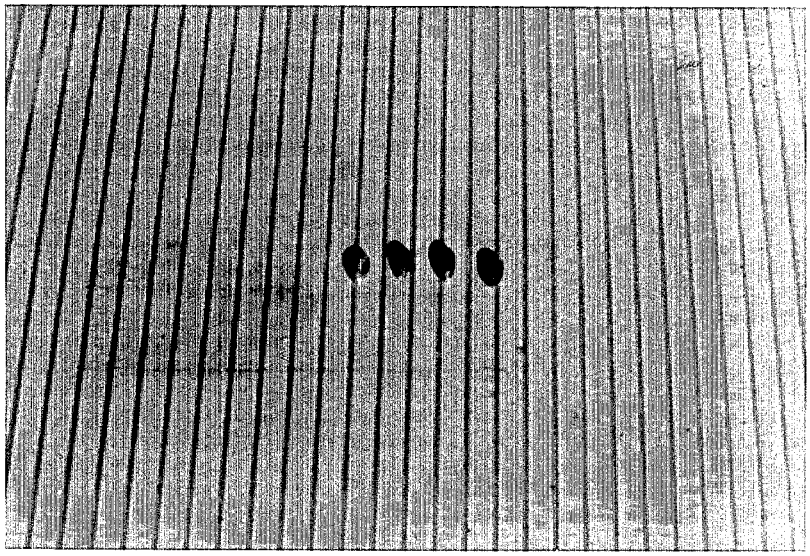
FIG. 8 shows seeds taken from Waliser Gala fruits.

*Fruit.*—Maturity when described — eating ripe. Size: Medium, uniform. Axial diameter: About 6.5 cm. Transverse diameter: From 6.5 to 7 cm. Form: Globose. Cavity: Symmetrical, round, slightly undulate, smooth. Base: Abrupt. Apex: Acuminate. Depth: About 2.2 cm. Breadth: About 2.4 cm. Markings: None. Basin: Symmetrical, rounded, wide, undulate, smooth, nonpubescent. Depth: About 0.8 cm. Markings: None. Stem: Medium stout, variable length and thickness. Length: About 2.4 cm. Breadth: About 0.2 cm. Calyx: Closed, persistent. Segments: Broadly lanceolate, reflexed from base at apex. Outer surface: Pubescent. Inner surface: Pubescent. Skin: Thin, smooth, glossy, waxed. Lenticels: Inconspicuous, many, small, even, more numerous toward calyx, circular, pale yellow (26-3). Ground color: Greenish-yellow (21-8). Color markings: Red (40-12) with light red pinstripes (38-11). Bloom: Wanting. Scarskin: Very light, white. General color effect: Bright red with faint small, narrow pinstripes (FIG. 6). Flesh: Juicy. Color: Satiny white (22-1). Texture: Firm, tender, fine crisp. Flavor: Subacid, sprightly, rich. Aroma: Agreeable, Weigela-like fragrance, distinct. Quality: Best. Core; Median. Bundle area: Medium small, oblate, symmetrical, halves of area equal. Bundles:

Inconspicuous, in one whorl. Core lines: Clasping. Cross-section: Indistinct. Calyx tube: Glabrous toward base, funnel form. Stem of funnel: Long; depth of tube to shoulder, about 0.5 cm; entire depth of funnel, about 1.2 cm. Styles: Present, united toward basae, glabrous at base to point of branching. Stamens: In one distinct whorl, median. Auxiliary cavity: Present. Seed cells: Axile, open, length, about 1.5 cm; breadth, about 0.5 cm.

What is claimed is:

1. A new and distinct variety of apple tree which is a mutation of the Royal Gala (Tenroy cultivar, U.S. Plant Pat. No. 4,121) substantially as herein shown and described, characterized particularly by a bright red color interspired with small, fine, light red pinstripes which color pattern develops very early in the Gala season and completely covers the fruits.

* * * * *